(12) United States Patent
Nagai

(10) Patent No.: US 6,411,834 B1
(45) Date of Patent: Jun. 25, 2002

(54) BIOLOGICAL SENSOR

(75) Inventor: Yuko Nagai, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 26 days.

(21) Appl. No.: 09/654,268

(22) Filed: Sep. 1, 2000

(30) Foreign Application Priority Data

Sep. 3, 1999 (JP) .......................................... 11-249671

(51) Int. Cl.$^7$ .............................. A61B 5/05; A61B 5/04
(52) U.S. Cl. ....................... 600/348; 600/353; 600/372; 600/373
(58) Field of Search ................................ 600/348, 345, 600/353, 373, 372

(56) References Cited

U.S. PATENT DOCUMENTS

| 4,273,134 | A | | 6/1981 | Ricciardelli | |
|---|---|---|---|---|---|
| 4,442,841 | A | * | 4/1984 | Uehara et al. | 600/360 |
| 4,474,183 | A | | 10/1984 | Yano et al. | |
| 4,750,494 | A | * | 6/1988 | King | 600/512 |
| 4,754,753 | A | * | 7/1988 | King | 600/512 |
| 4,953,553 | A | | 9/1990 | Tremulis | |
| 5,028,395 | A | * | 7/1991 | Sebille et al. | 600/367 |
| 5,361,762 | A | * | 11/1994 | Günter | 600/372 |
| 6,134,478 | A | * | 10/2000 | Spehr | 600/373 |

FOREIGN PATENT DOCUMENTS

| JP | 58-97346 | 6/1983 | ........... A61B/10/00 |
|---|---|---|---|
| JP | 4-32985 | 6/1992 | ......... G01N/27/414 |

* cited by examiner

*Primary Examiner*—Kevin Shaver
*Assistant Examiner*—Navin Natnithithadha
(74) *Attorney, Agent, or Firm*—Sughrue Mion, PLLC

(57) ABSTRACT

An annul protecting portion 23 having a thickness larger than the thickness of a sensor sensitive portion 1 is provided in such a manner as to surround the sensor sensitive portion 1, the sensor sensitive portion 1 together with the protecting portion 23 is placed between living tissues, so as to ensure that the gate portion 7 is not subjected to an external pressure by coming into contact with the living tissues. Further, outer peripheries of lead wires 4 on the sensor sensitive portion 1 side are covered with a plasticity material 24 woven into a tubular shape by a metal wire such as a stainless steel wire, and is grounded together with the metallic protecting portion, so as not to be subjected to induction noise. Further, the metal wire is bent to hold the sensor sensitive portion 1 at a suitable angle.

9 Claims, 5 Drawing Sheets

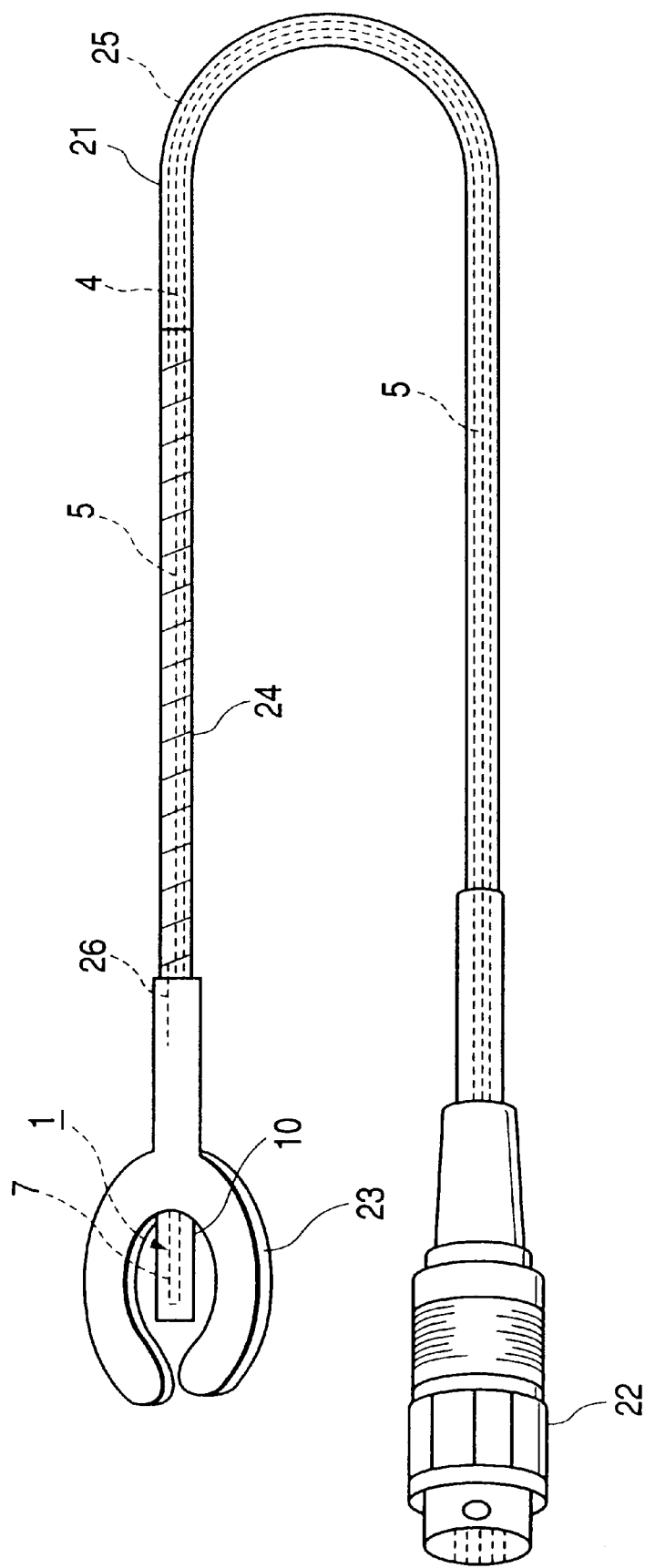

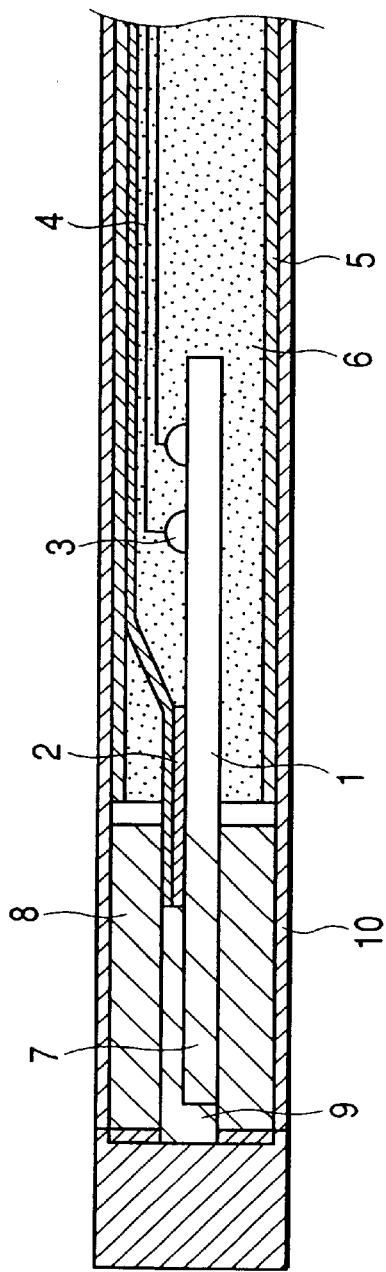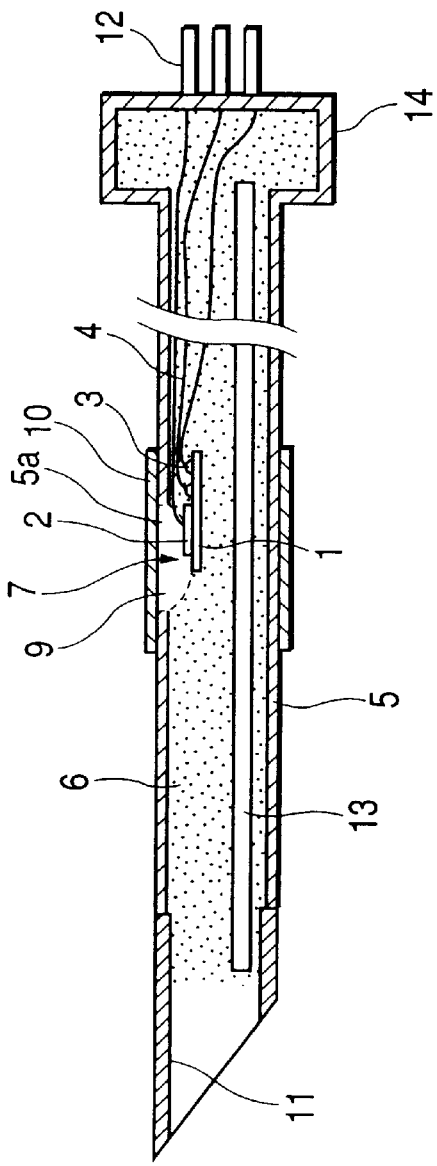

BIOLOGICAL SENSOR

BACKGROUND OF INVENTION

1. Field of Invention

The present invention relates to a biological sensor which is capable of stably measuring the concentration of a gas and ions in living tissues.

2. Related Art

The measurement of the concentration of a gas, such as carbon dioxide and ammonia gas, is important in industrial applications. In recent years emphasis has come to be placed on the measurement of a gas concentration and an ion concentration in an organism in the fields of medicine and physiology. In this measurement, a very small biological sensor which can be used by being inserted in cells or a blood vessel is required.

As sensors of this type, sensors having various structures have been proposed. For example, a gas sensor disclosed in Examined Japanese Patent Publication Hei. 4-32985. FIG. 3 is a cross-sectional view illustrating the construction of one example of the gas sensor proposed therein. In FIG. 3, an ion sensor of a gate-insulated field-effect transistor structure (hereafter referred to as the ISFET) 1, a reference electrode 2, and lead wires 4 connected to electrode portions 3 of the ISFET 1 are embedded in an electrical insulating resin 6 inside a tube 5. A gate portion 7, which is an ion sensitive portion of the ISFET 1, and a portion of the reference electrode 2 are inserted in a hollow portion of a single porous hollow fiber 8, and are covered in the porous hollow fiber 8. The porous hollow fiber 8 and a space between the porous hollow fiber 8 and the ISFET 1 is filled with a space absorbing fluid 9. The porous hollow fiber 8 is further covered with a homogeneity membrane 10.

With the gas sensor constructed as described above, since the porous hollow fiber 8 is fabricated in advance by a fiber forming technology, its shape and the distribution of pores can be easily made constant. For this reason, it is possible to reduce the variations in the characteristics of the gas sensor. Further, since the porous hollow fiber 8 is not fluid and can retain a substantially fixed shape, the amount of change in the characteristics of the sensor is small. Further, by covering a distal end of the ISFET 1 with the porous hollow fiber 6, the breaking of the homogeneity membrane 10 by the distal end of the ISFET 1 can be suppressed to a certain degree.

FIG. 4 is a cross-sectional view illustrating the construction of another conventional example of this type of sensor.

This sensor is disclosed in unexamined Japanese Patent Publication Sho. 58-97346. In FIG. 4, portions corresponding to the portions of the conventional example shown in FIG. 3 are denoted by the same reference numerals, and a description thereof will be omitted, as required. The characteristic feature of this conventional example lies in that a needle 11 is provided at the distal end of the tube 5, that the ISFET 1 and the reference electrode 2 are accommodated in an opening 5a formed in side wall of the tube 5 in such a manner as to come into contact-with the gas absorbing fluid 9, and that the opening 5a is covered by the gas permeable homogeneity membrane 10. Connector pins 12 are disposed at a rear end of the tube 5, and the lead wires 4 are connected to the connector pins 12. It should be noted that reference numeral 13 denotes a reinforcing core wire embedded inside the tube 5 between its distal end portion and a connector 14.

According to the gas sensor constructed as described above, by inserting the tube 5 into living tissues through the needle 11, a state-of close contact between the ISFET 1 and the tissues is established, so that it is possible to measure the gas concentration in the tissues with excellent reproducibility.

However, according to the gas sensor disclosed in Examined Japanese Patent Publication Hei. 4-32985, since porous hollow fiber 8 is likely to be deformed by the external pressure since it has plasticity, and since the gate portion 7 of the ISFET 1 is subjected to pressure from the living tissues through the porous hollow fiber 8, the output of the sensor becomes unstable. Further, since the ISFET 1 and the reference electrode 2 are formed of rigid materials, if they are subjected to an external force, there are possibilities that these members become broken and that the gas permeable membrane 10 is punctured thereby, causing damage to the sensor structure.

On the other hand, according to the gas sensor disclosed in Unexamined Japanese Sho. 58-97346, since the tube 5 is punctured into the living tissues through the needle 11, there has been a drawback in that the living tissues can be damaged.

In addition, with the above-described two conventional examples, since no consideration is given to the fixation of the sensor to the object, there has been a problem in that the sensor is likely to come off.

Furthermore, since a shielding structure is not provided for protecting from induction noise an unillustrated leading portion for leading a signal detected by the ISFET 1 to the outside, the sensor is susceptible to the effect of such as an electric cautery, so that there has been a problem in that the signal output changes.

SUMMARY OF INVENTION

The invention has been devised in view of the above-described circumstances, and its object is to provide a biological sensor capable of stably measuring a gas or ion concentration in living tissues without damaging the living tissues. Another object of the invention is to provide a biological sensor which can be easily secured at a measurement region of an object.

To attain the above objects, in the invention according to first aspect of the present invention, there is provided a biological sensor including a sensor sensitive portion for detecting a gas concentration or an ion concentration in a living tissue as the sensor sensitive portion is brought into contact with the living tissue, and a leading portion for leading to an outside a signal representing the gas concentration or the ion concentration detected by the sensor sensitive portion, provided in that a protecting portion having a thickness larger than the thickness of the sensor sensitive portion surrounds the sensor sensitive portion, and is fixed to the leading portion.

Biological sensor according to second aspect of the present invention, the protecting portion is formed of a high rigidity resin or metal which is difficult to absorb a gas or ions.

Biological sensor according to third aspect of the present invention, an outer periphery of the leading portion on a sensor sensitive portion side is covered with a plasticity material.

Biological sensor according to a fourth aspect of the present invention, the plasticity material has a metal member for covering the leading portion.

Biological sensor according to a fifth aspect of the present invention, the metal member is electrically grounded.

Biological sensor according to a sixth aspect of the present invention, the protecting portion is formed of a metal, and the metal member is further electrically connected to the protecting portion.

Biological sensor according to a seventh aspect of the present invention, the protecting portion is formed of a metal, and is electrically grounded.

Biological sensor according to a eighth aspect of the present invention, the plasticity material is defined by a metal wire having plasticity and a flexible synthetic resin tube.

In biological sensor according to the first and second aspects of the present invention, since the sensor sensitive portion for detecting the concentration of a gas or ions from living tissues is surrounded by the protecting portion having a thickness larger than the thickness of the sensor sensitive portion, by placing the protecting portion between the living tissues, a signal representing the concentration of a gas or the like in the living tissues can be outputted stably without causing the living tissues to come into direct contact with the sensitive portion.

In biological sensor according to the third and fourth aspects of the present invention, since the outer periphery of the leading portion is covered with the plasticity material, the leading portion can be fixed stably by being curved at an angle conforming to a measurement region.

In biological sensor according to fourth to seventh aspects, since the metallic protecting portion and the metal member are electrically grounded, it is possible to reduce induction noise due to high frequencies from an electric cautery or the like to which the leading portion is subjected, thereby making it possible to obtain a stable signal output. Namely, since the induction noise caused by electric cautery is likely to affect the sensor signal through the leading portion, the grounding of the metal member of the plasticity portion produces a large effect. In cases where the plasticity material does not include a metal member, it is possible to enhance the effect by leading the grounding line of the protecting portion together with the tube. Further, in order to obtain an enhanced effect, it is preferable to include a metal member in the plasticity material and ground both the metallic protecting portion and the plasticity material.

In biological sensor according to the eighth aspect of the present invention, by covering the metal wire having plasticity with the flexible synthetic resin tube, it is possible to prevent the danger of elution of metal ions and leakage current into the living tissue and the like.

In biological sensor according to a ninth aspect of the present invention, the protecting portion prevents an excess pressure from being applied to the sensor sensitive portion when the biological sensor is disposed in the organism, and the protecting portion causing the gas to diffuse toward the sensor sensitive portion from at least two directions.

BRIEF DESCRIPTION OF DRAWINGS

FIG. 2 is a perspective view illustrating a second example of the construction in accordance with the embodiment of a sensor for an organism of the invention;

FIG. 3 is a cross-sectional view illustrating the construction of an example of a conventional sensor for an organism;

FIG. 4 is a cross-sectional view illustrating the construction of another example of the conventional sensor for an organism;

FIG. 6 is showing a cross sectional view taken along line A—A in FIG. 1; and.

DETAILED DESCRIPTION OF PREFERRED EMBODIMENT

Figure 1:
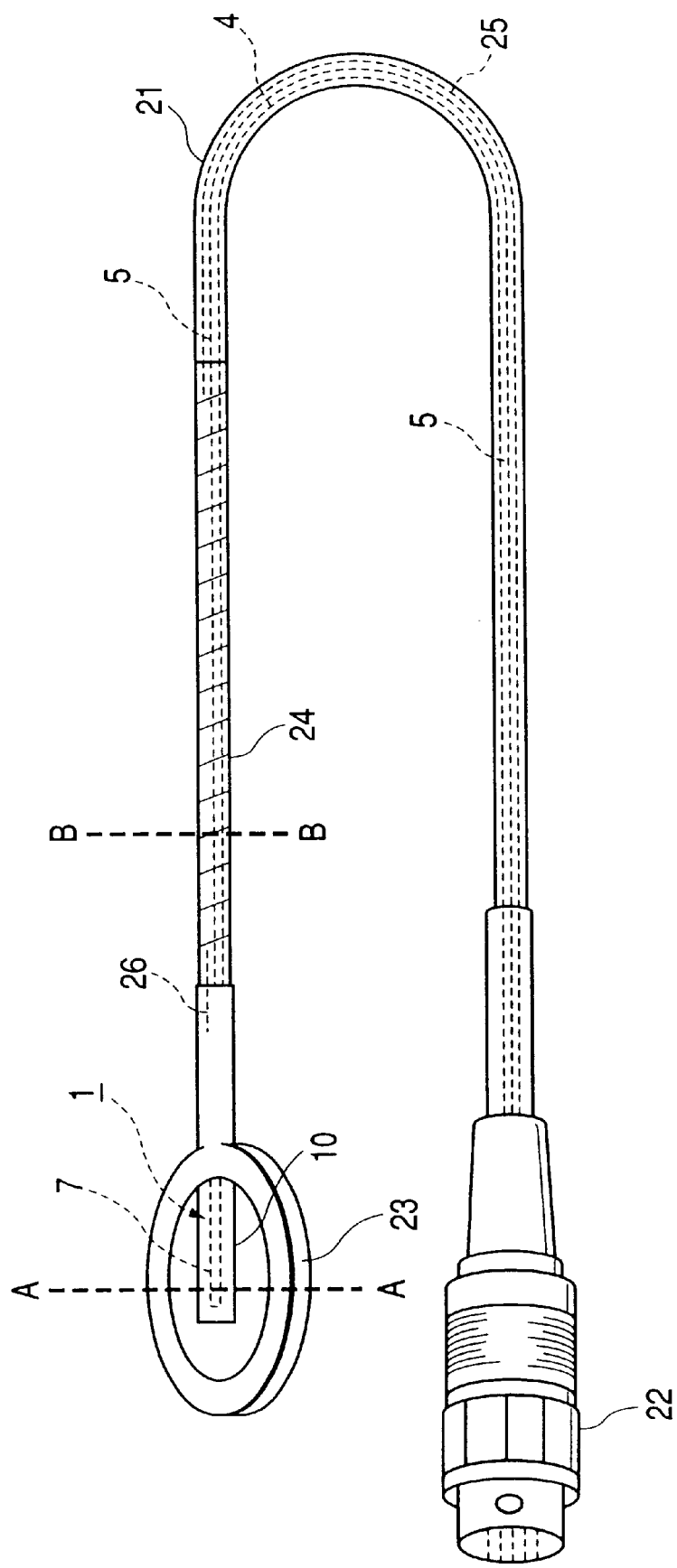
FIG. 1 is a perspective view illustrating a first example of the construction in accordance with an embodiment of a sensor for an organism of the invention.

Referring now to the drawings, a description will be given of an example of the construction of an embodiment of a biological sensor in accordance with the invention. FIG. 1 is a perspective view illustrating a first example of the construction in accordance with an embodiment of the invention. In FIG. 1, portions corresponding to the portions of the conventional example are denoted by the same reference numerals, and a description thereof will be omitted, as required.

An ISFET 1 is provided with a reference electrode 2 and electrode portions 3, although not shown, in the same way as the conventional example shown in FIG. 3, and lead wires 4 are connected to the electrode portions 3, respectively. A gate portion 7 at a distal end of the ISFET 1 and a portion of an outer periphery of the reference electrode 2 are covered with a gas-permeable silicone membrane 10. In addition, a tube 5 serving as a leading portion for accommodating the lead wires 4 is covered with a cable cover 21, and the lead wires 4 are connected to a connector 22 provided in a proximal end of the cable cover 21.

Figure 6:
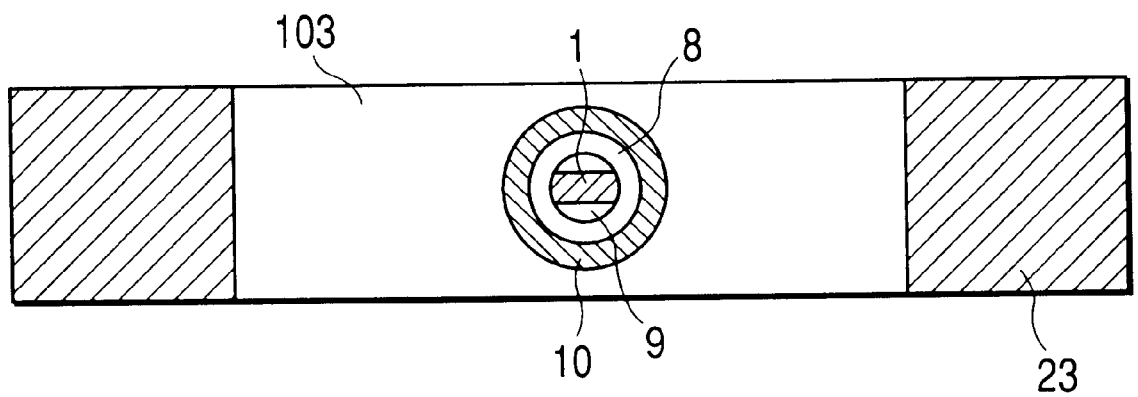

A proximal portion of an annular protecting portion 23 surrounding the gate portion 7 is fixed to one end of the ISFET 1 on the electrode portion 3 side shown in FIG. 3. The thickness of the protecting portion 23 is set to be larger than the thickness of the ISFET 1 covered with the silicone membrane 10, such that when the protecting portion 23 is placed between living tissues, the external pressure from the tissues is not directly applied to the silicone membrane 10. Both sides of the sensor sensitive portion and the protecting portion 23 are placed between living tissues and the gas is diffused from the living tissues from the both directions for the purpose that the change in the gas concentration in an area surrounding the sensor sensitive portion well follows up the change in the gas concentration of the living tissues. And the space 103 in FIG. 6 is provided between the sensor sensitive portion and the protecting portion 23 so as not to hamper the diffusion of the gas but the space 103 is provided to such an extent that the protecting portion 23 is able to support the living tissues so that an excess external pressure will not be applied from the living tissues to the sensor sensitive portion. The protecting portion 23 is formed of a resin which is difficult to absorb gas and ions and has high hardness, such as a polymer, polycarbonate, Teflon, polypropylene, and epoxy, a metal such as stainless steel, or such a metal with a resin coated thereon.

Figure 5:
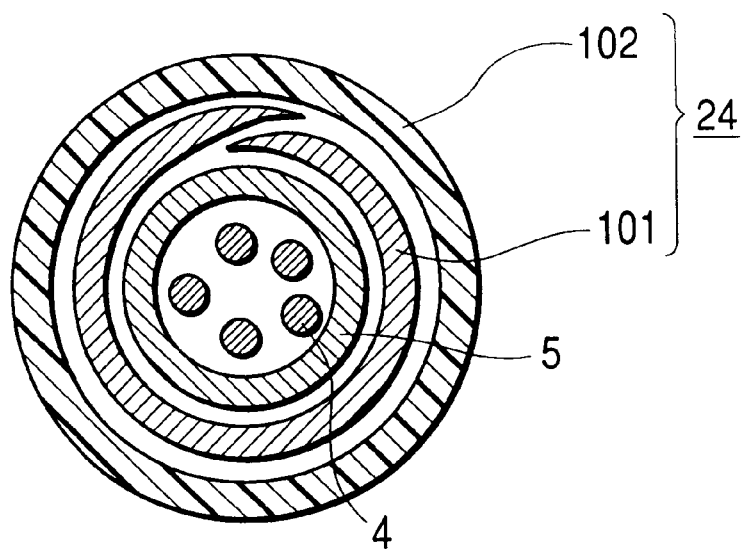
FIG. 5 is showing a cross sectional view taken along line B—B in FIG. 1.

As shown in FIG. 5, which is a cross-sectional view taken along line B—B in FIG. 1, the lead wires 4 for leading the output of the ISFET 1 are encased in the tube 5 formed of a synthetic resin tube which is difficult to expand or contract such as a nylon tube or a Teflon tube, the tube 5 is woven into a tubular shape or wound spirally by a metal wire 101 such as a stainless steel wire having plasticity as a metal member, and is further covered with a synthetic resin tube 102 with plasticity such as a silicone tube or a polyvinyl chloride tube, thereby forming a plasticity material 24. The plasticity material 24 can be fabricated by molding by inserting in advance the metal wire 101 in the synthetic resin at. the time of molding the synthetic resin tube 102, or also by bonding the metal wire 101 to the inner side of the synthetic resin tube by an adhesive agent. A portion of the protecting portion 23 is pushed into one end of the plasticity material 24 on its inner periphery, and is bonded thereto by an adhesive agent. In FIG. 5, a space is defined between the lead wires 4 and the tube 5. The present invention is not limited by this embodiment. It is applicable for filling with the synthetic resin or the like with a plasticity function.

When the protecting portion 23 is formed of a metal, an electrical connecting portion 26 is provided by welding or soldering one end of a metal wire 25 on the inner side of a proximal portion of the protecting portion 23. The metal wire 25 together with the tube 5 is passed through the cable cover 21, and its other end is connected to the connector 22 provided in the proximal end of the cable cover 21, and is grounded. The connecting portion 26 may be electrically connected to the metal wire constituting the plasticity material 24.

Figure 7:
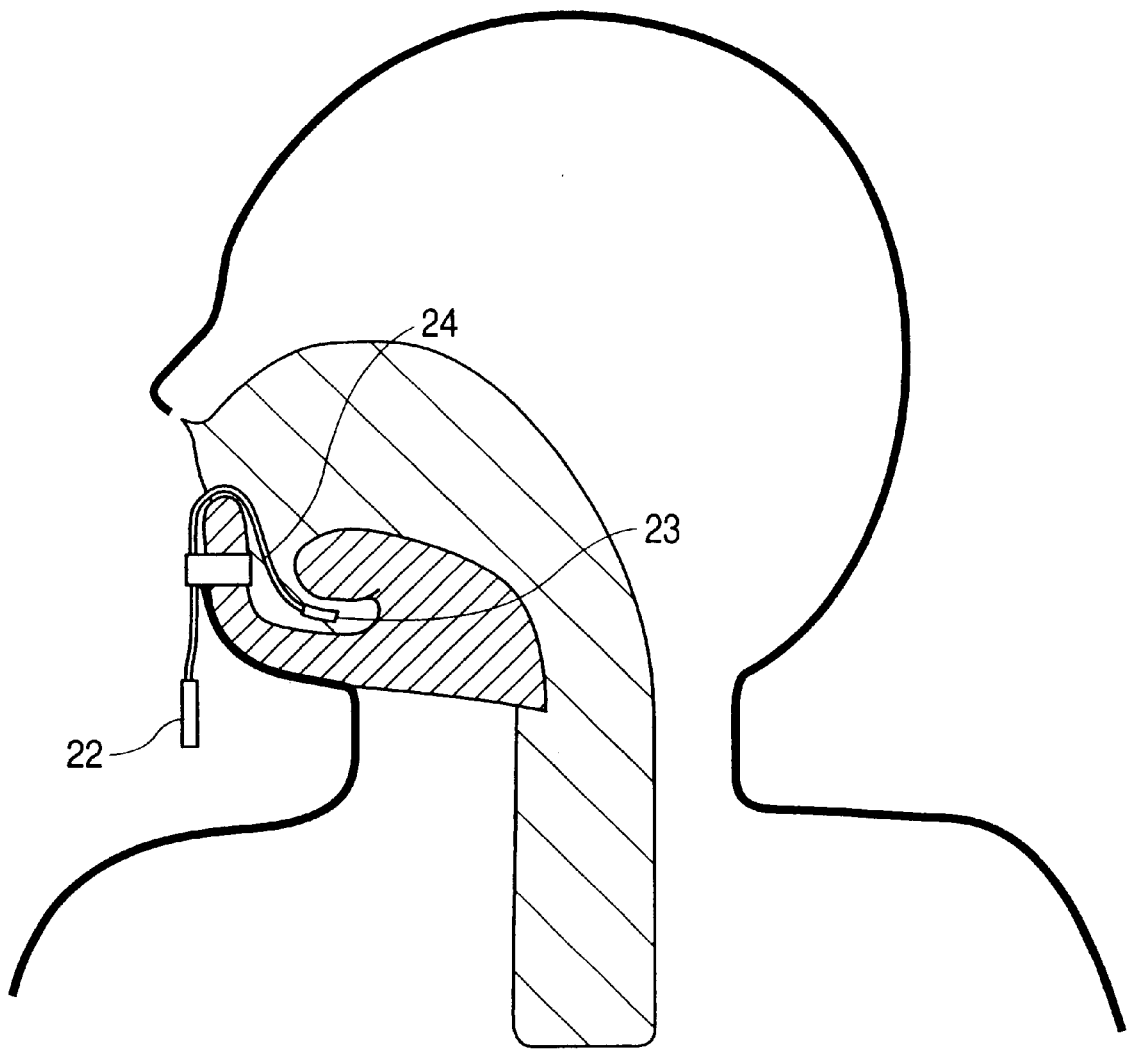
FIG. 7 is showing a schematic view of a sensor is interposed in sublingual tissue.

Next, a description will be given of a method of using the biological sensor constructed as described above. As shown in FIG. 7, the protecting portion 23 is interposed in sublingual tissue (intraoral hypoglossal tissues) or organ tissue at the time of laparotomy, and the plasticity material 24 is bent at an angle for facilitating the sensor, and is bonded and secured to the skin and the like in its vicinity with an adhesive tape. In this state, a gas or a body fluid in the living tissue is introduced to the gate portion 7 through an open portion in the center of the protecting portion 23, and the concentration of a gas such as $CO_2$ or the concentration of ions such as pH is detected.

According to this embodiment, since the living tissue is not directly brought into contact with the ISFET 1 including the gate portion 7 which is a sensor sensitive portion, the external pressure is not applied, and a signal representing the gas concentration can be outputted stably. In addition, since the ISFET 1 can be easily fixed in the form of being made to conform to a measurement region, the sensor can be held stably without damaging the living tissues, and a signal output can be stabilized.

Since a leading portion for leading the sensor signal is susceptible to induction noise caused by am electric cautery, the grounding of the metal member of the plasticity material 24 produces a large effect. Further, in order to increase this effect, it is preferable to ground both the metallic protecting portion 23 and the metal portion of the plasticity material 24. In cases where the plasticity material 24 does not include a metal member, it is possible to enhance the effect by leading the grounding line of the protecting portion 23 together with the tube 5 which is a leading portion.

Although, in the above-described embodiment, a description has been given of the case in which the protecting portion 23 is formed in a circular form, the shape of the protecting portion 23 is not limited to the same. For example, the protecting. portion 23 may be formed in a substantially U-shaped form as shown in a second example of the construction shown in FIG. 2. FIG. 6 is showing a cross sectional view taken along line A—A in FIG. 1. This figure shows the thickness relationship between protecting portion 23 and the sensor sensitive portion 24. Further, the configuration of the ISFET 1 is not limited to the one shown in FIG. 1, and another configuration may be adopted if it has a similar function. Furthermore, in a case where the sensor can be easily attached to living tissues stably, the plasticity material 24 may be omitted, or a flexible synthetic resin tube may be merely used instead of the plasticity material 24.

Moreover, the invention is also applicable to cases where the sensor is other than the ISFET 1, and may be also applied to a micro pH sensor using glass electrodes, an ion sensor and a gas sensor using Severinghaus-type $CO_2$ electrodes and optical fibers, and an oxygen sensor using the basic principle of a Clark-type electrode.

As described above, in accordance with the present invention, since the protecting portion having a thickness larger than the thickness of the sensor sensitive portion is provided so as to surround the sensor sensitive portion, by placing the sensor between living tissues, a signal representing the concentration of a gas or the like in the living tissues can be outputted stably without causing the living tissues to come into direct contact with the sensitive portion and without applying an external pressure to the sensitive portion.

In accordance with the present invention, since the outer periphery of the leading portion is covered with the plasticity material, the leading portion can be fixed stably to the organism by being curved at an angle conforming to a measurement region, and the signal output can be stabilized without damaging the living tissues.

In accordance with the present invention, since the metal wire having plasticity is covered with the flexible synthetic resin tube, it is possible to prevent the danger of elution of metal ions and leakage current into the living tissues and the like.

In accordance with the present invention, since the metallic protecting portion and the metal member are grounded, it is possible to reduce induction noise due to high frequencies from an electric cautery or the like to which the leading portion is subjected, thereby making it possible to further stabilize the signal output.

In accordance with the present invention, since the structure in which both sides of the sensor sensitive portion and the protecting portion are interposed between living tissues, there is an advantage in that since the gas is diffused from the living tissues from both directions, the change in the gas concentration in an area surrounding the sensor sensitive portion well follows up the change in the gas concentration of the living tissues, so that the response speed of the sensor improves.

As conditions for obtaining the aforementioned effect, it is preferable to provide a space defined between the sensor sensitive portion and the protecting portion so as not to hamper the diffusion of the gas, but the space is preferably provided to such an extent that the protecting portion is able to support the living tissues so that an excess external pressure will not be applied from the living tissues to the sensor sensitive portion.

What is claimed is:

1. A biological sensor comprising:
    a sensor sensitive portion for detecting at least one of a gas concentration and an ion concentration in a living tissue by bringing said sensor sensitive portion into contact with the living tissue;
    a leading portion for leading to an outside a signal representing at least one of the gas concentration and the ion concentration detected by said sensor sensitive portion; and
    a protecting portion having a thickness larger than the thickness of said sensor sensitive portion and surrounding said sensor sensitive portion, and said protecting portion being fixed to said leading portion,
        wherein a portion of said protecting portion that surrounds said sensor sensitive portion has a flat, planar shape.

2. The biological sensor according to claim 1, wherein said protecting portion is formed of at least one of a high-hardness resin and metal which is hard to absorb at least one of a gas and ions.

3. The biological sensor according to claim 1, wherein an outer periphery of said leading portion on a sensor sensitive portion side is covered with plasticity material.

4. The biological sensor according to claim 3, wherein said plasticity material has a metal member for covering said leading portion.

5. A biological sensor comprising:
a sensor sensitive portion for detecting at least one of a gas concentration and an ion concentration in a living tissue by bringing said sensor sensitive portion into contact with the living tissue;
a leading portion for leading to an outside a signal representing at least one of the gas concentration and the ion concentration detected by said sensor sensitive portion; and
a protecting portion having a thickness larger than the thickness of said sensor sensitive portion surrounding said sensor sensitive portion, and said protecting portion being fixed to said leading portion,
wherein an outer periphery of said leading portion on a sensor sensitive portion side is covered with plasticity material,
wherein said plasticity material has a metal member for covering said leading portion,
wherein said metal member is electrically grounded.

6. A biological sensor comprising:
a sensor sensitive portion for detecting at least one of a gas concentration and an ion concentration in a living tissue by bringing said sensor sensitive portion into contact with the living tissue;
a leading portion for leading to an outside a signal representing at least one of the gas concentration and the ion concentration detected by said sensor sensitive portion; and
a protecting portion having a thickness larger than the thickness of said sensor sensitive portion surrounding said sensor sensitive portion, and said protecting portion being fixed to said leading portion,
wherein said protecting portion is formed of a metal, and said metal member is further electrically connected to said protecting portion.

7. A biological sensor comprising:
a sensor sensitive portion for detecting at least one of a gas concentration and an ion concentration in a living tissue by bringing said sensor sensitive portion into contact with the living tissue;
a leading portion for leading to an outside a signal representing at least one of the gas concentration and the ion concentration detected by said sensor sensitive portion; and
a protecting portion having a thickness larger than the thickness of said sensor sensitive portion surrounding said sensor sensitive portion, and said protecting portion being fixed to said leading portion,
wherein said protecting portion is formed of a metal and is electrically grounded.

8. A biological sensor comprising:
a sensor sensitive portion for detecting at least one of a gas concentration and an ion concentration in a living tissue by bringing said sensor sensitive portion into contact with the living tissue;
a leading portion for leading to an outside a signal representing at least one of the gas concentration and the ion concentration detected by said sensor sensitive portion; and
a protecting portion having a thickness larger than the thickness of said sensor sensitive portion surrounding said sensor sensitive portion, and said protecting portion being fixed to said leading portion
wherein an outer periphery of said leading portion on a sensor sensitive portion side is covered with plasticity material,
wherein said plasticity material is defined by a metal wire having plasticity and a flexible synthetic resin tube, and said metal wire is covered with said flexible synthetic resin tube.

9. A biological sensor comprising:
a sensor sensitive portion for detecting at least one of a gas concentration and an ion concentration in a living tissue by bringing said sensor sensitive portion into contact with the living tissue; and
a leading portion for leading to an outside a signal representing at least one of the gas concentration and the ion concentration detecting by said sensor sensitive portion,
a protecting portion provided to prevent an excess pressure from being applied to said sensor sensitive portion when said sensor for an organism is disposed in the organism, and sail protection portion causing the gas to diffuse toward said sensor sensitive portion from at least two directions,
wherein a portion of said protecting portion surrounds said sensor sensitive portion and has a flat, planar shape.

* * * * *